(12) United States Patent
Borsari

(10) Patent No.: US 10,463,142 B2
(45) Date of Patent: Nov. 5, 2019

(54) TWISTED IN WIRE BRUSH HAVING A MOLDED TIP AND METHOD OF ASSEMBLY THEREFOR

(71) Applicant: SANDERSON-MACLEOD, INC., Palmer, MA (US)

(72) Inventor: Mark N. Borsari, Wilbraham, MA (US)

(73) Assignee: Sanderson-MacLeod, Inc., Palmer, MA (US)

( * ) Notice: Subject to any disclaimer, the term of this patent is extended or adjusted under 35 U.S.C. 154(b) by 288 days.

(21) Appl. No.: 15/446,379

(22) Filed: Mar. 1, 2017

(65) Prior Publication Data

US 2017/0258214 A1 Sep. 14, 2017

Related U.S. Application Data

(60) Provisional application No. 62/306,861, filed on Mar. 11, 2016.

(51) Int. Cl.
| | | |
|---|---|---|
| *A46B 3/00* | (2006.01) | |
| *A46B 3/18* | (2006.01) | |
| *A61B 90/70* | (2016.01) | |
| *A46B 5/00* | (2006.01) | |
| *A46B 9/02* | (2006.01) | |
| *A46D 1/00* | (2006.01) | |
| *A46D 3/00* | (2006.01) | |
| *F41A 29/02* | (2006.01) | |
| *A61B 1/12* | (2006.01) | |

(52) U.S. Cl.
CPC .............. *A46B 3/18* (2013.01); *A46B 5/0012* (2013.01); *A46B 5/0087* (2013.01); *A46B 9/021* (2013.01); *A46B 9/026* (2013.01); *A46D 1/0207* (2013.01); *A46D 3/00* (2013.01); *A61B 1/122* (2013.01); *A61B 90/70* (2016.02); *F41A 29/02* (2013.01); *A46B 2200/1053* (2013.01); *A46B 2200/3013* (2013.01); *A61B 2090/701* (2016.02)

(58) Field of Classification Search
CPC .......... A46B 3/18; A46B 5/0012; A46D 3/00; A45D 40/26
See application file for complete search history.

(56) References Cited

U.S. PATENT DOCUMENTS

| | | |
|---|---|---|
| 1,967,597 A | 7/1934 | Schwartz |
| 2,633,592 A | 4/1953 | Meyer |
| (Continued) | | |

FOREIGN PATENT DOCUMENTS

| | | | | |
|---|---|---|---|---|
| EP | 1510149 A1 | * | 3/2005 | ............... A46B 3/18 |
| GB | 2064314 | * | 6/1981 | |
| (Continued) | | | | |

OTHER PUBLICATIONS

International Search Report dated May 19, 2017 Based Off of Application No. PCT/US2017/020136.

*Primary Examiner* — Michael D Jennings
(74) *Attorney, Agent, or Firm* — Grogan, Tuccillo & Vanderleeden, LLP

(57) ABSTRACT

A brush includes a wire core, a round tip formed on a distal end of the wire core, the round tip being unitary with the wire core section and being formed by melting or welding a portion of the wire core at the distal end, and a molded tip attached to the wire core at the distal end via a ball-and-socket connection.

11 Claims, 18 Drawing Sheets

(56) References Cited

U.S. PATENT DOCUMENTS

| | | | |
|---|---|---|---|
| 5,135,112 A * | 8/1992 | Kamen | A45D 33/006 |
| | | | 132/294 |
| 6,465,758 B1 | 10/2002 | Ham | |
| 6,717,092 B2 | 4/2004 | Obata et al. | |
| 7,121,284 B2 | 10/2006 | Gueret | |
| 2004/0158945 A1 | 8/2004 | Moore | |
| 2010/0192320 A1 | 8/2010 | Borsari et al. | |

FOREIGN PATENT DOCUMENTS

| | | | | |
|---|---|---|---|---|
| WO | WO-2013034638 A1 * | 3/2013 | | A46B 5/0066 |
| WO | 2016135270 A1 | 9/2016 | | |

* cited by examiner

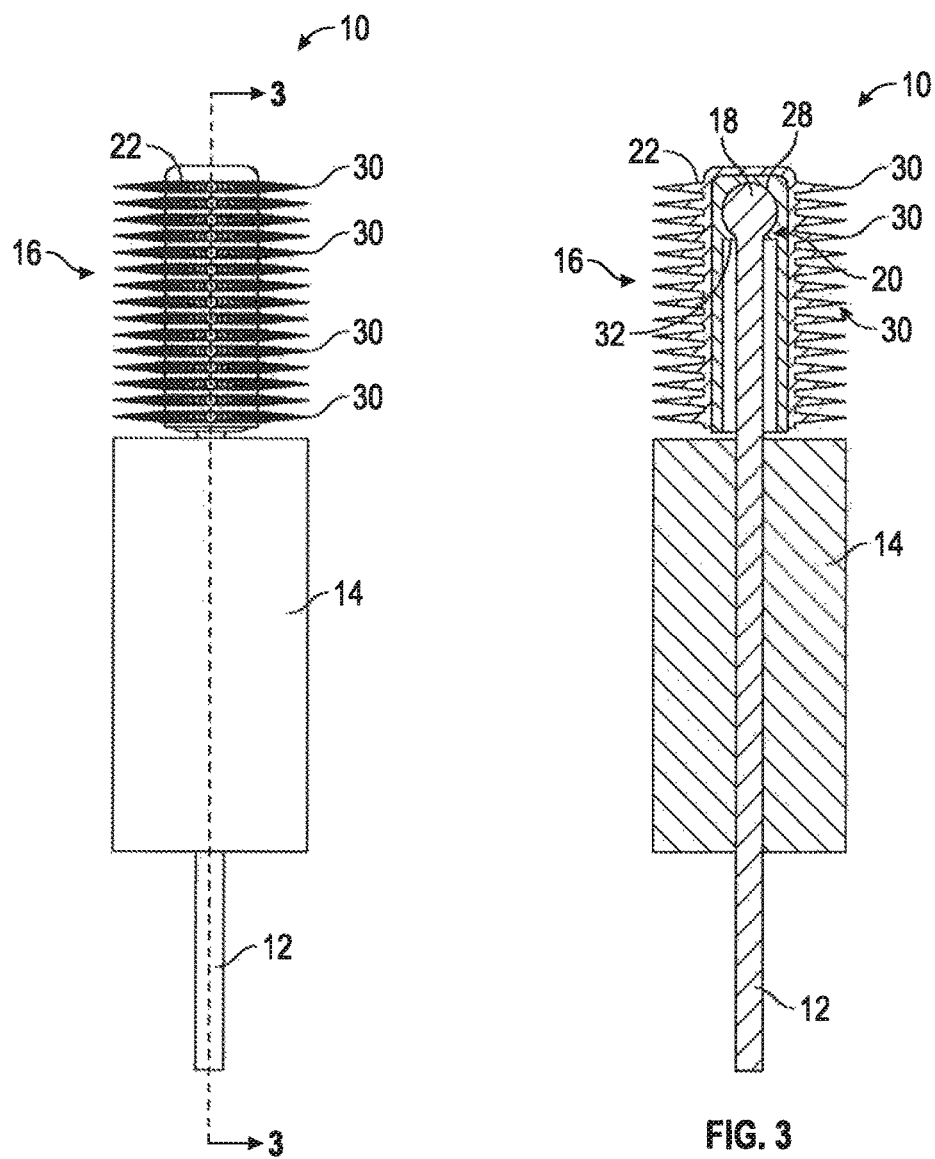

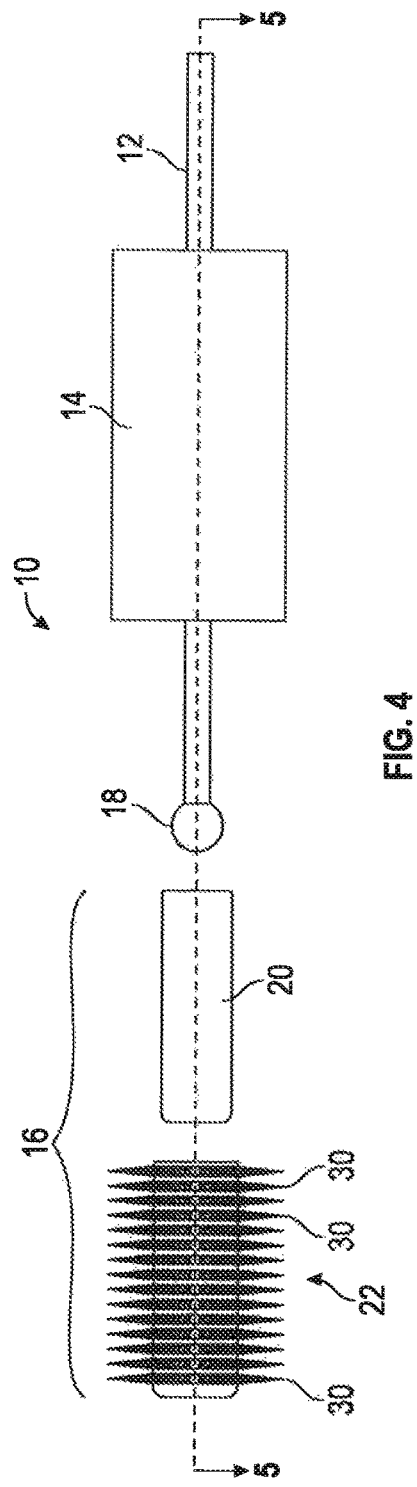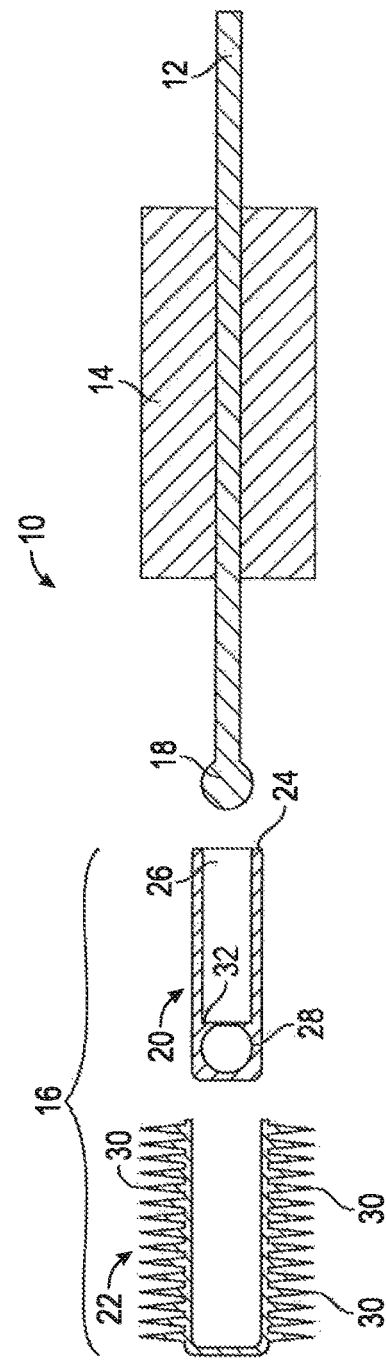
FIG. 4
FIG. 5

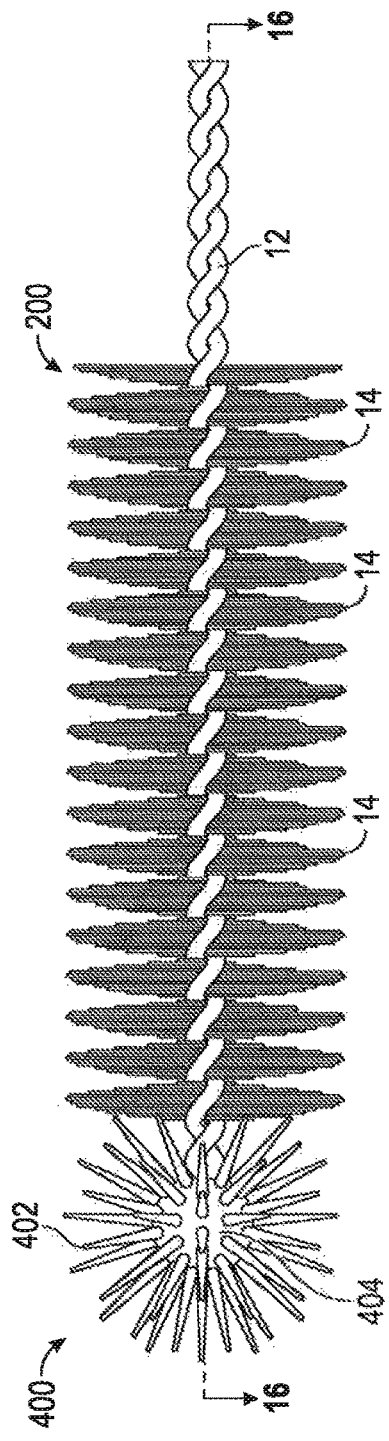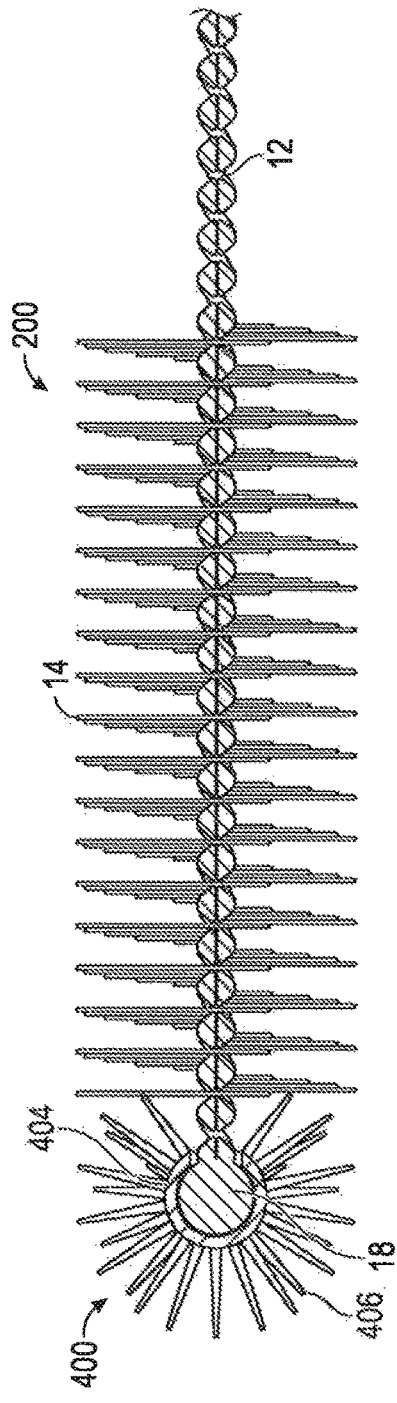
FIG. 15
FIG. 16

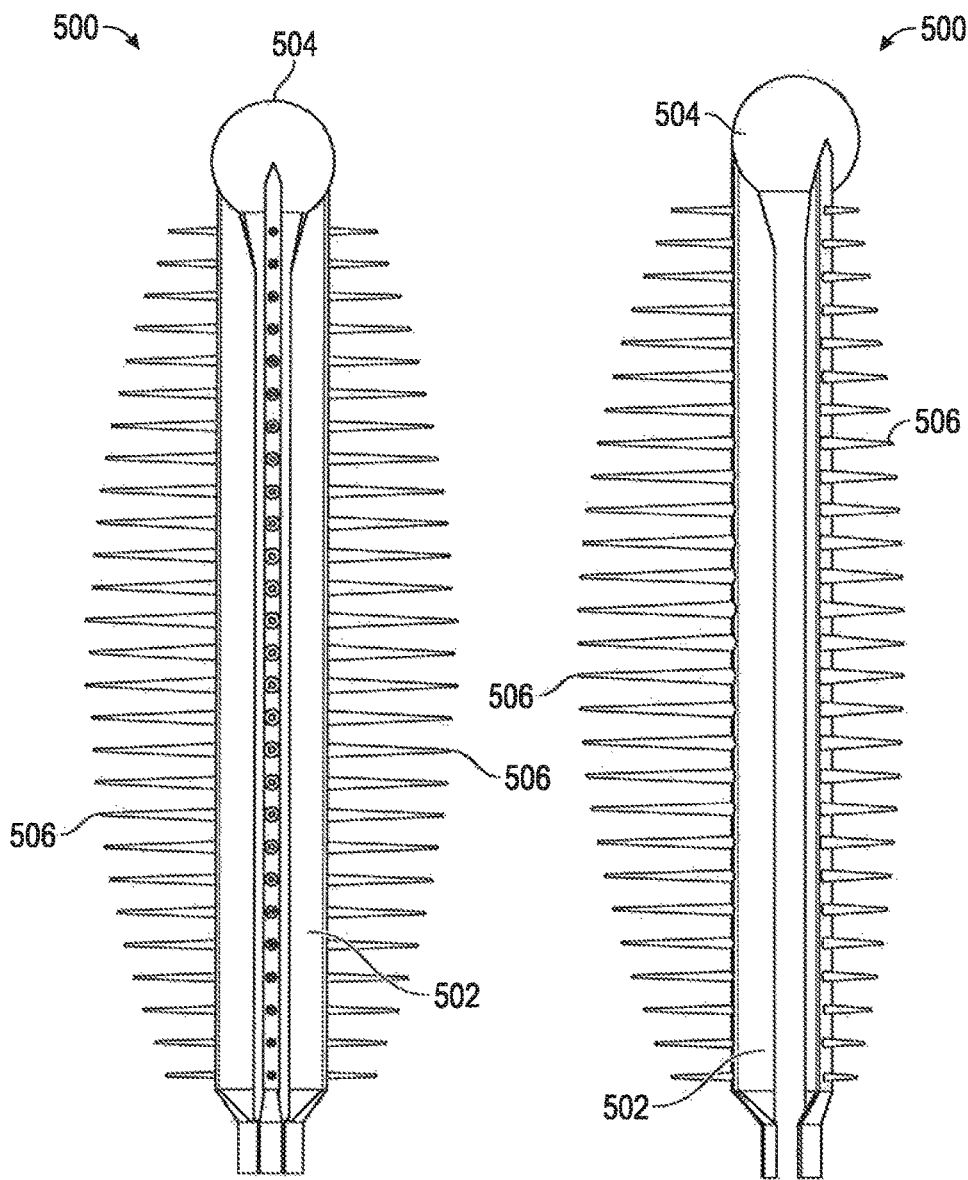

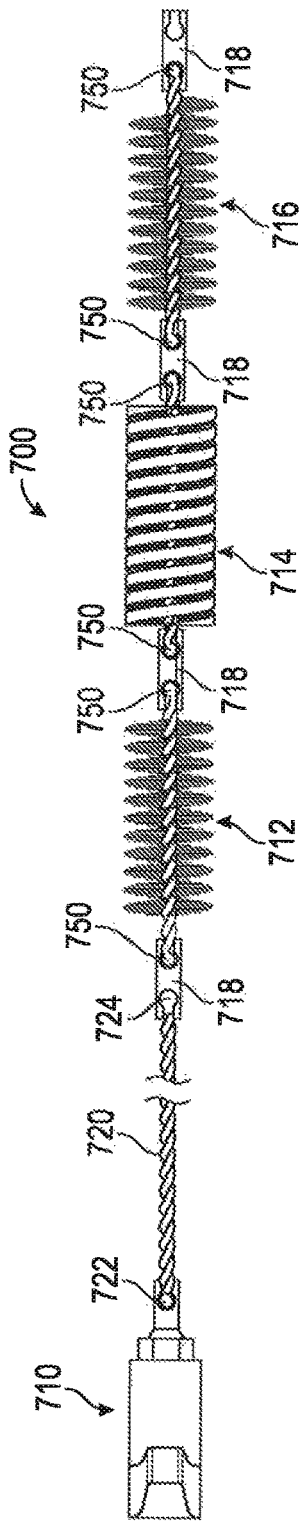
FIG. 30
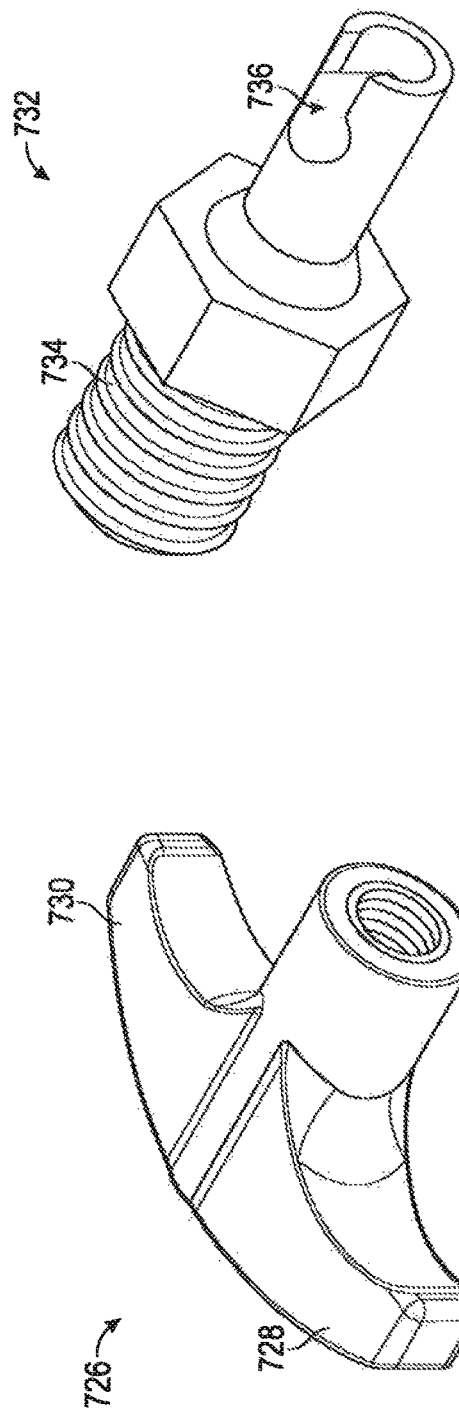
FIG. 31
FIG. 32

TWISTED IN WIRE BRUSH HAVING A MOLDED TIP AND METHOD OF ASSEMBLY THEREFOR

CROSS-REFERENCE TO RELATED APPLICATIONS

This application claims the benefit of U.S. Provisional Application Ser. No. 62/306,861, filed on Mar. 11, 2016, which is hereby in incorporated by reference herein in its entirety.

FIELD OF THE INVENTION

The present invention relates generally to twisted in wire brushes and, more particularly, to a twisted in wire brush having a molded applicator or cleaning tip, and related method of assembly.

BACKGROUND OF THE INVENTION

Brushes for cleaning the inner surfaces of vessels and/or for applying makeup or other personal care product compositions are well known in the art. One type of such brush is the twisted in wire brush, which is commonly used in a variety of applications including, but not limited to, hole cleaning, sanding, deburring or lubricating, tube or vessel cleaning, beaker cleaning, pistol, rifle and shotgun cleaning, medical equipment cleaning, medical and dental procedures, medical applications and the application of personal care products including mascara and the like. Twisted in wire brushes are also known as spiral, tube flue, bottle, pipe, boiler or power brushes, and are generally comprised of a plurality of bristles held and secured by a pair of twisted metal wires which form the core of the brush. The bristles are often formed from some type of acrylic fiber and extend radially from the core or longitudinal axis of the brush, generally resulting in a roughly cylindrical appearance. It will be readily appreciated, however, that the bristles may be formed from any suitable material including metal, such as stainless steel, brass or bronze, nylon, Teflon, polypropylene, horse or hog hair, depending on the specific use. Moreover, depending on the specification application, the ends of the brush can also vary. For example, a brush may have a rough-cut tip, a rounded tip or a bristled or fan tip, and can have a long end or handle, a short end, or a finished end having various configurations such as a ring or loop.

Other brushes, in addition to, or instead of having bristles held in place by the twisted wire core, may utilize applicator or cleaning tips comprised of molded plastic or rubber parts, including plastic or rubber bristles, that are attached to the core section of the brush. Existing methods of attaching such molded tips to the core section of the brush, however, may often be unreliable. For example, such molded tips may be prone to detachment from the core section of the brush, particularly when used in applications such as medical applications and gun cleaning where a reasonable force is necessary to effectuate cleaning, deburring, etc. In such applications, the forces generated by the cleaning motion can sometimes cause detachment of the tip and unraveling of the twisted wire core, which can lead to exposure of often sharp or abrasive ends of core wires, making the vessel more prone to scratching and other damage. In addition, detachment of the tip may result in the leaving of undesirable debris, e.g., bristles or caps, within the vessel that is cleaned or deburred. There is therefore a need to increase the structural strength of such brushes so as to prevent unraveling in applications where a reasonable force is needed to effectuate cleaning, deburring, lubricating, etc.

In view of the problems associated with known techniques and methods for forming twisted in wire brushes and, more particularly, for forming brushes with molded plastic or rubber applicator or cleaning tips, there is a need for an improved brush that is less prone to tip detachment, and which can be quickly and easily assembled.

SUMMARY OF THE INVENTION

In view of the foregoing, it is an object of the present invention to provide a brush.

It is another object of the present invention to provide a twisted in wire brush.

It is another object of the present invention to provide a twisted in wire brush having a molded applicator or cleaning tip.

It is another object of the present invention to provide a twisted in wire brush having a molded applicator or cleaning tip that can be quickly and easily integrated with the wire core.

It is another object of the present invention to provide a twisted in wire brush having a molded applicator or cleaning tip that is held in secure engagement with the twisted wire core.

According to an embodiment of the present invention, a brush includes a wire core, a round tip formed on a distal end of the wire core, the round tip being unitary with the wire core and being formed by melting or welding a portion of the wire core at the distal end, and a molded tip attached to the wire core at the distal end via a ball-and-socket connection.

According to another embodiment of the present invention, a method of forming a twisted in wire brush having a molded tip includes providing a brush with a wire core, melting a portion of the wire core at an end thereof, by applying an energy source to said end, to form a rounded tip, and securing a molded tip to the end of the wire core through a ball-and-socket type connection.

According to yet another embodiment of the present invention, a brush includes a first brush member including a wire core having a proximal end and a distal end, and a generally spherical tip formed on at least one of said proximal end and said distal end of said wire core, a second brush member including a wire core having a proximal end and a distal end, and a generally spherical tip formed on at least one of said proximal end and said distal end of said wire core, and a linking member having a body having a first socket formed in a first end of said body and a second socket formed in a second end of said body. The generally spherical tip of said first brush member is received in said first socket of said linking member and the generally spherical tip of said second brush member is received in said second socket of said linking member such that said first brush member and said second brush member are linked together in a serial configuration.

BRIEF DESCRIPTION OF THE DRAWINGS

The present invention will be better understood from reading the following description of non-limiting embodiments, with reference to the attached drawings, wherein below:

FIG. 2 is a side elevational view of the brush of FIG. 1.

FIG. 3 is a cross-sectional view of the brush of FIG. 1, taken along line A-A of FIG. 2.

FIG. 4 is an exploded view of the brush of FIG. 1.

FIG. 5 is a cross-sectional, exploded view of the brush of FIG. 1, taken along line B-B of FIG. 4.

FIG. 19 is a perspective view of an alternative brush tip, according to an embodiment of the present invention.

FIG. 15 is a side elevational view of the brush of FIG. 14.

FIG. 16 is a cross-sectional view of the brush of FIG. 14, taken along line A-A of FIG. 15.

FIGS. 17-19 are various views of an alternative brush tip, according to an embodiment of the present invention.

FIGS. 20-22 are various views of the brush tip of FIG. 17, shown attached to the rounded tip of a twisted in wire brush.

FIG. 30 is a cross-sectional view of the brush of FIG. 29.

FIG. 31 is a perspective view of a gripping portion of a handle of the brush of FIG. 29.

FIG. 32 is a perspective view of a coupling member of the handle of the brush of FIG. 29.

DETAILED DESCRIPTION OF THE PREFERRED EMBODIMENTS

The present invention is directed to a cleaning or applicator device, more specifically a brush, having a molded plastic or rubber tip, and further to a method of manufacturing or assembling the same. The brush is especially adapted to be used for cleaning the interior surfaces of vessels, such as in medical applications, for example, the cleaning of catheters, arthroscopic devices, cameras, etc., and for use in cleaning pistols, rifles and shotguns. In addition, the brush is adapted to be used for applying compositions, such as in personal care applications, for example, the application of mascara.

Figure 1:
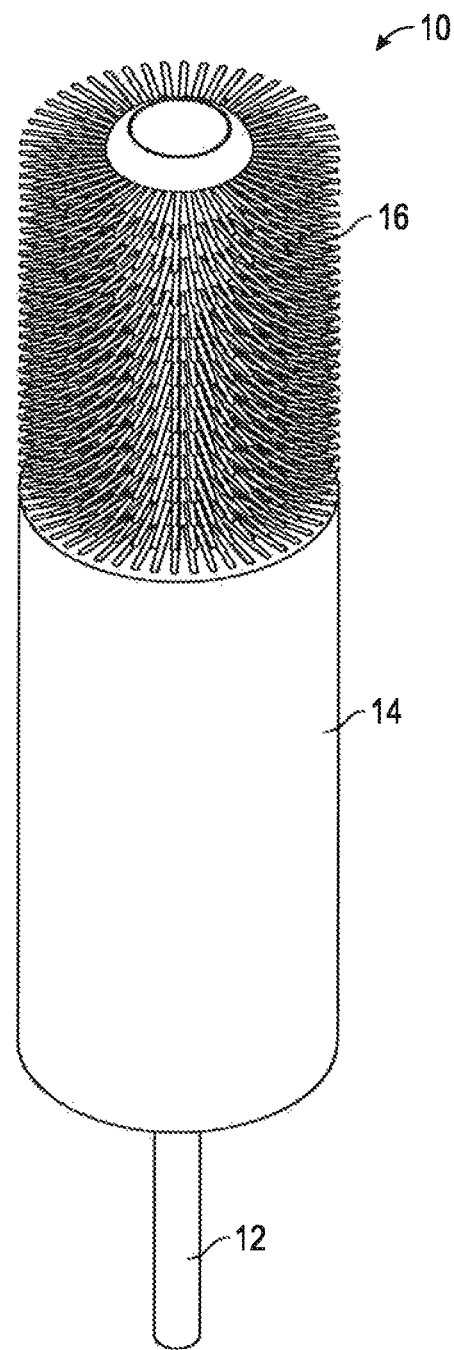
FIG. 1 is a perspective view of a brush having a molded tip, according to an embodiment of the present invention.

Referring now to FIGS. 1 and 2, a brush 10 according to an embodiment of the present invention is illustrated. As illustrated therein, the brush 10 includes a core wire section 12 defining a stem, a plurality of fibers or bristles 14 secured by the core wire section 12 and extending radially therefrom, and a molded tip 16 attached to the core wire section 12 at a distal end thereof. A handle (not shown) may secured to the end of the stem opposite the molded tip 16, for allowing a user to grasp and manipulate the brush 10.

In an embodiment, the brush may be fabricated in the customary manner by using a pliable metallic wire, reversibly folded back upon itself. A plurality of bristles of predetermined length are placed between the two coextensive leg portions of the wire. The wire is then twisted to form the core 12 of helical configuration, which grips the bristles at the midpoint of their length, causing the filaments 14 to be crimped and folded in half. The outer tips of the bristles 14 define a roughly cylindrical shape of predetermined diameter, or a conical shape. The bristles 14 may be further trimmed to arrive at various additional shapes. While this is an exemplary method of forming a twisted in wire brush, it will be readily appreciated that any fabrication process or method for forming twisted in wire brushes known in the art may be employed, without departing from the scope of the present invention.

For example, it will be readily appreciated that a plurality of wires may be used in place of the single wire described above. In such a situation, the plurality of wires may be placed adjacent one another, a plurality of bristles placed between the wires, and the wires twisted together to form a core of helical configuration and to anchor the bristles in place. Other methods and configurations of forming wire brushes and twisted in wire brushes are known in the art and may be incorporated in the current design without departing from the scope of the present invention.

In an embodiment, the helical metallic wire core 12 is made up of at least two coextensive leg portions which are twisted around each other in a helical configuration and which anchor the bristle block. The metallic wire core 12 may be comprised of nickel alloys, titanium alloys, stainless steel alloys, carbon steel alloys, cobalt alloys or aluminum alloys, although other metals or metal alloys may be used without departing from the scope of the present invention. In other embodiments, the core wire section may include a single length of wire, and the brush need not include bristles held in place by the wire core.

Turning now to FIGS. 3, 4 and 5, the distal end of the core wire section/stem 12 is formed with an integral, substantially spherical tip or ball 18 that defines a retaining device or anchoring point for the molded tip 16, as discussed hereinafter. The integral ball 18 may be formed on the distal end of the wire core by melting or welding of the distal end of the core section 12 after twisting of the core 12 to anchor the bristles 14, as disclosed in U.S. Pat. No. 8,850,650, which is hereby incorporated by reference herein in its entirety. In particular, to form the smooth and substantially rounded ball 18 on the bristle end of the core 12, the present invention uses high-energy fusion welding to "melt" the wire core 12 of the brush 10 at the distal end thereof. For example, in the case of a "broken nose" brush, welding is used to melt the end surfaces of the coextensive leg portions of the pre-constructed core wire section into a consistent, smooth and inseparable rounded tip. In the case of a "continuous end" brush, welding the distal end also melts and eliminates any sharp or uneven edges, and likewise forms a consistent, smooth and inseparable rounded tip. In addition, melting of the core section 12 at the distal end also eliminates any contaminant trapping voids that may be present. Once fused, the coextensive leg portion are unable to be separated from one another, and the rounded tip is also inseparable from the core section 12. Importantly, welding or melting of the distal end of the core wire section 12 results in a metallurgical bond between the ball 18 and the core wire section 12 of the brush 10.

Specific welding technologies such as Laser, Gas Tungsten Arc Welding (GTAW), Plasma Arc Welding and Electron Beam Welding may be used to melt the bristle end 120 to form the spherical tip 18. In particular, the preferred parameter range is 0.001 Milliamps to 200 Amps for Gas Tungsten Arc Welding, 15 Kv-200 Kv for Electron Beam Welding and 1 Amp-200 Amps for Plasma Arc Welding, although other parameters may be used. For Laser technology, near ultra violet and/or near infra red laser sources are preferred, although other wavelengths may be used to achieve the objects of the present invention. While the embodiments described herein disclose a spherical tip, in certain embodiments, the tip may be generally spherical (i.e., not entirely spherical). The tip may be spherical to an extent that it can be retained within a correspondingly shaped (e.g., ball-shaped socket), as discussed hereinafter.

It is a further advantage of the present invention that the spherical tip 18, once formed, is incapable of being separated from the wire core 12, as the core 12 and tip 18 is a unitary welded or melted piece, i.e., the core wire section 12 and the spherical tip 18 are homogeneous (having been formed from the same piece of material, without the addition of any other quantity of material). A further advantage of the melted tip 18 formed on the brush 10 of the present invention is that such tip increases the structural strength of the brush itself, which aids substantially in ensuring that the leg portions of the wire core 12 do not become unraveled.

In connection with the above, the integral, spherical tip 18 also provides a mechanism by which the molded tip 16 may be attached and anchored to the distal end of the brush 10. For example, in an embodiment, the molded tip 16 may include a molded core section 20 and a molded bristle section 22 received on the molded core section 20. As best illustrated in FIGS. 4 and 5, the molded core section 20 is a generally cylindrical part having an end 24 having an opening 26 therein that extends through the core section to a substantially spherical cavity 28 opposite the end 24. The spherical cavity 28 defines a socket that is substantially sized and shaped to closely receive the spherical ball 18 of the core section 12 of the brush 10 therein, as discussed in detail hereinafter. In an embodiment, the molded core section 20 of the molded tip 16 is formed from plastic or other polymer.

As also shown in FIGS. 4 and 5, the molded bristle section 22 of the molded tip 16 defines a generally hollow body having a plurality of bristles 30 extending outwardly therefrom. The interior of the hollow body is sized and shaped so as to closely receive the molded core section 20 therein. In the preferred embodiment, the molded bristle section 22 of the molded tip 16 is formed from rubber.

In an embodiment, the molded core section 20 may be secured to the molded bristle section 22 by any means known in the art, such as utilizing adhesives and the like. In other embodiments, the molded bristle section 22 and the molded core section 20 may be formed as a single, integral part. The molded bristle section 22 and molded core section 20 may be formed utilizing any molding process known in the art such as, for example, injection molding, rotational molding, thermoforming, etc.

In an embodiment, after the molded tip 16 is formed by joining the molded bristle section 22 with the molded core section 20, the tip 16 may be secured to the wire core 12 of the brush by sliding the molded tip 16 over the distal end of the core 12 until the spherical ball 18 contacts the shoulder 32 between the socket 28 and the cylindrical cavity that extends through the core section 20. Axial pressure is then utilized to force the spherical ball 18 into seated position within the socket 28, forming a ball-and-socket type joint or connection. In this position, the geometry of the ball 18 and socket 28 prevents decoupling of the molded tip 16 from the core section 12 of the brush 10, and securely holds the molded tip 16 on the distal end of the core section 12. As shown in FIGS. 3 and 5, the socket 28 may be formed at a distal end of the molded tip 16 such that at least a portion of the wire core section 12 is received within the passageway in the molded tip 16. This configuration provides a more robust connection between the molded tip 16 and wire core 12, minimizing lateral or pivoting movement of tip 16 relative to the wire core 12. In certain embodiments, it is contemplated that various molded tips corresponding to various functions may be selectively attached and detached from the wire core 12 to provide a level of customization and functionality heretofore not seen in the art.

Importantly, this ball-and-socket type connection provides for a cost effective and efficient means of assembling a molded plastic or rubber bristle block onto the distal end of a twisted in wire brush. In addition, the ball-and-socket attachment mechanism provides for a secure connection that is less prone to decoupling than existing methods and devices. In contrast to existing devices, in the rare event that the molded tip does become decoupled from the core wire section, the smooth surface of the integral tip 18 of the core wire section prevents the brush from scratching, scarring or damaging sensitive surfaces, particularly before such decoupling is detected by a user.

Moreover, in yet another embodiment of the present invention, a method is provided for forming a protective tip on a cleaning apparatus. Such method involves manufacturing a brush, in particular a twisted in wire brush, as hereinbefore described. The method further comprises the steps of positioning the bristle end of the cleaning apparatus or brush adjacent to an electrode or laser, shielding the bristle block, and "melting" a pre-constructed core wire section of the brush into a consistent, smooth, unitary and inseparable rounded tip. This rounded tip, once formed, is unable to be separated from the wire core, thus reducing the risk of cleaning surface damage, as hereinbefore described. In addition, the method further includes attaching a molded tip having a plurality of bristles to the rounded tip of the brush by pushing the molded tip onto the rounded tip of the core until the rounded tip of the core is received in a socket within the molded tip.

While the embodiments described above contemplate the attachment of a molded rubber bristle block to the distal end of a twisted in wire brush, the present invention is not so limited in this regard. In particular, the brush having the ball-and-socket attachment mechanism of the present invention may be utilized in a variety of applications, to secure a variety of attachments to the distal end of a wire core section of a brush having an integral, rounded tip. For example, the present invention contemplates use in cosmetic applications such as for attaching overmold parts to twisted in wire brushes for nail enamel and mascara application, in medical applications including endoscopy, cytology, general cleaning, stylets, etc., gun care applications including swabs and brushes, and general cleaning applications. As indicated above, the integral ball 18 of the core section 12 of the wire brush 10 may be utilized to attach various attachments to the distal end of the brush 10, and is not limited to attaching bristle sections or the like. For example, in an embodiment, the ball 18 may be utilized to attach a dome or disc shaped diaphragm or squeegee to a wire core section, to be utilized for cleaning interior surfaces or evenly applying a composition to such interior surfaces.

Figure 6:
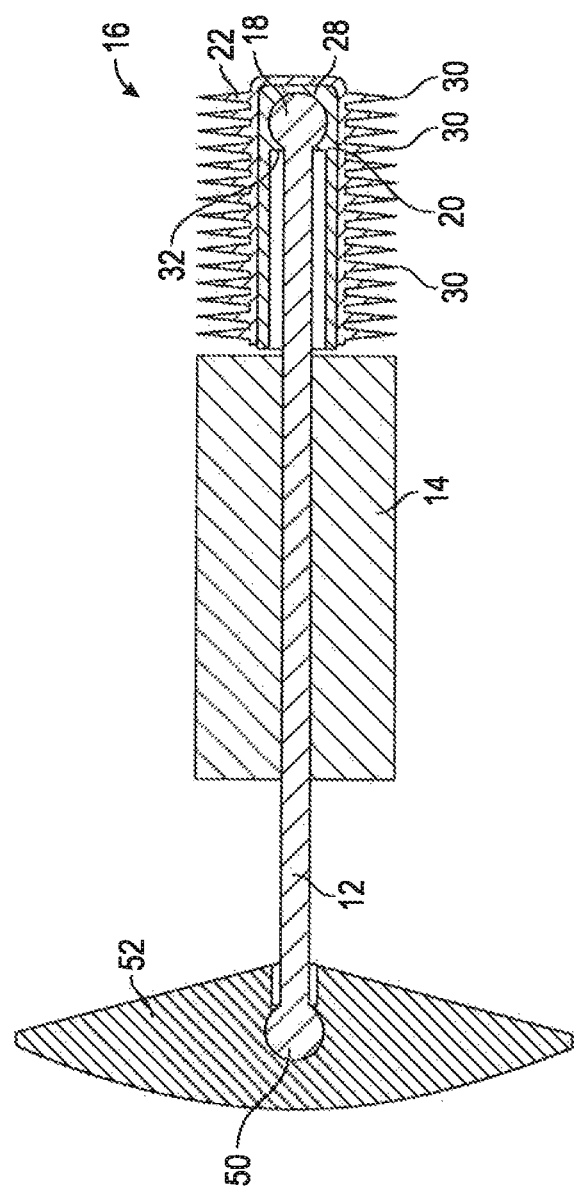
FIG. 6 is a cross-sectional view of a brush having dual molded tips, according to an embodiment of the present invention.
Figure 7:
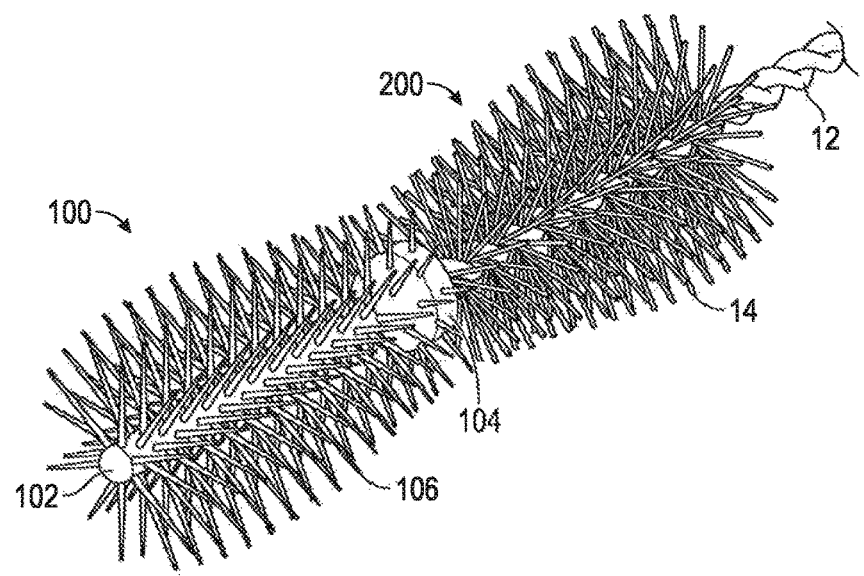
FIG. 7 is a perspective view of a twisted in wire brush having an alternative tip, according to an embodiment of the invention.
Figure 8:
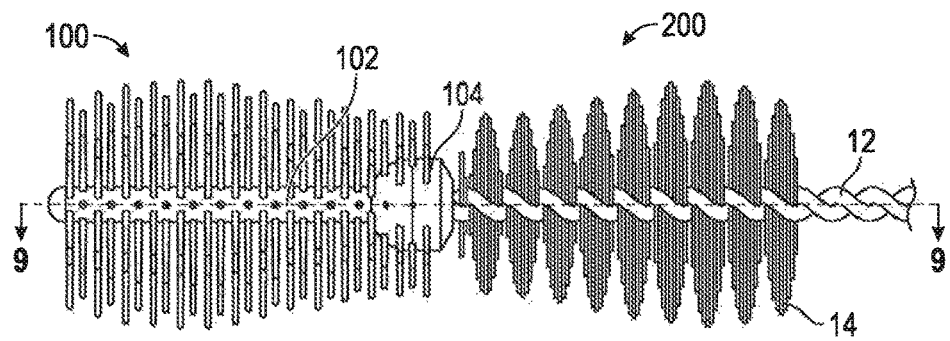
FIG. 8 is a side elevational view of the brush of FIG. 7.
Figure 9:
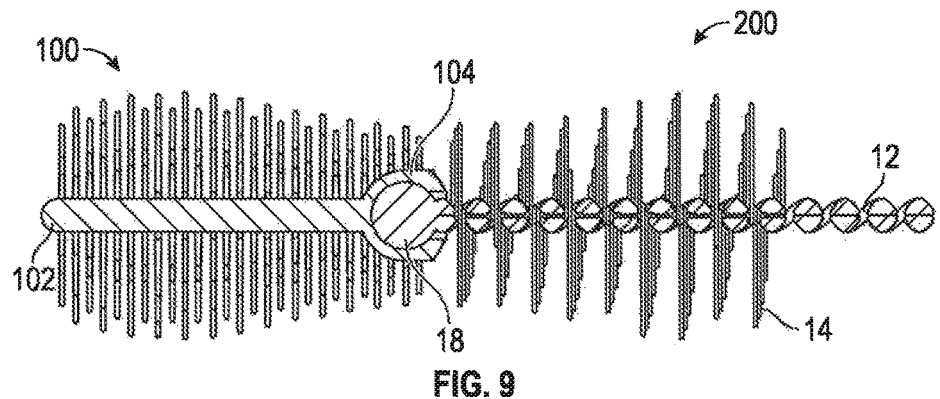
FIG. 9 is a cross-sectional view of the brush of FIG. 7, taken along line A-A of FIG. 8.

Referring to FIG. 6, it is also contemplated that the proximal end of the core wire section opposite the bristle block (e.g., the handle end) may also be melted to form a second rounded, unitary tip 50 to which a second molded tip 52 or other accessory may be attached via a similar ball-and-socket type connection. The second molded tip, for example, may have a different bristle configuration than the molded tip on the distal end of the brush (e.g., shorter or denser bristles), or may be a different accessory altogether (e.g., a diaphragm 52 or squeegee). The brush of the present invention may therefore provide for dual functions or uses, obviating the need to use multiple, distinct brushes to perform differing functions.

Figure 10:
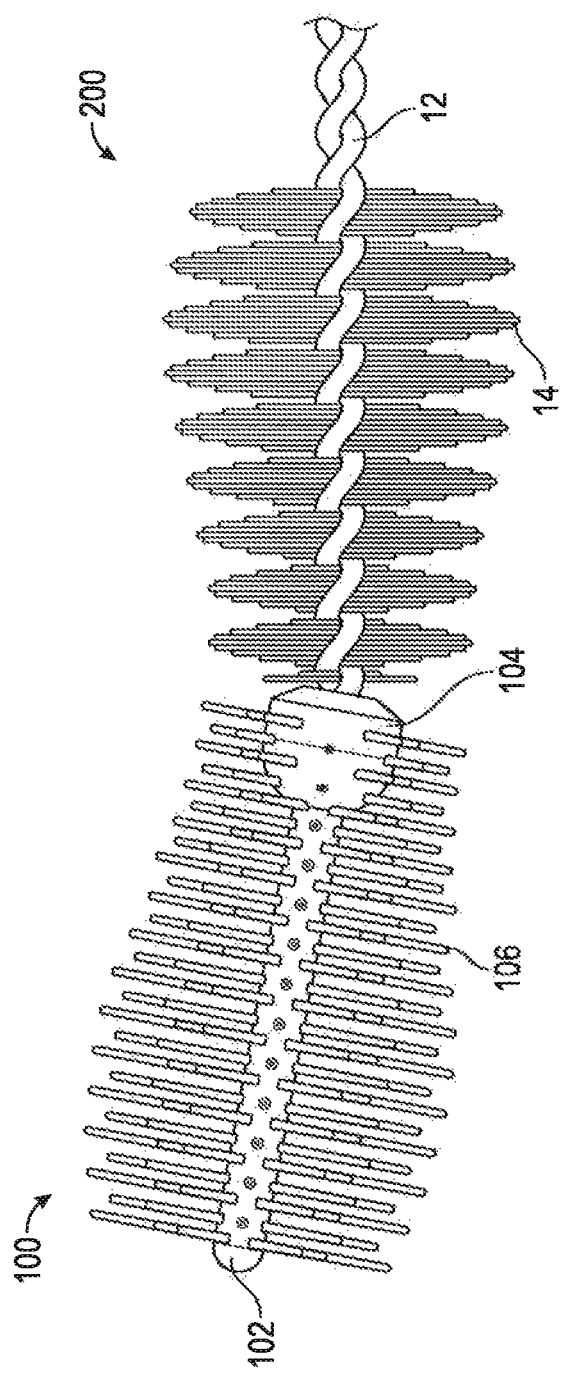
FIG. 10 is another perspective view of the brush of FIG. 7.

FIGS. 7-10 illustrate an alternative molded brush tip 100 attached to the spherical or ball-shaped tip 18 of a twisted in wire brush 200. The twisted in wire brush 200, is formed in the manner, and has the same configuration, as the twisted in wire brush discussed above. As shown therein, the brush tip 100 is a single molded piece having a core section 102 including a ball shaped socket 104, and a plurality of bristles 106 connected to, and extending from, the core section 102. In contrast to the tip 16 described above, the socket 102 of the brush tip 100 is located at a proximal end of the tip 100 (i.e., rather than at a distal end). The tip 18 of the brush 200 is received in the socket 104 of the brush tip 200. As illustrated in FIGS. 7-10, the connection point between the brush tip 100 and the brush 200 is at the midpoint of the assembled brush. As shown in FIG. 10, this permits the brush tip 100 to pivot relative to the brush 200 (i.e., the articulated ball-and-socket joint permits pivoting about such joint).

Figure 11:
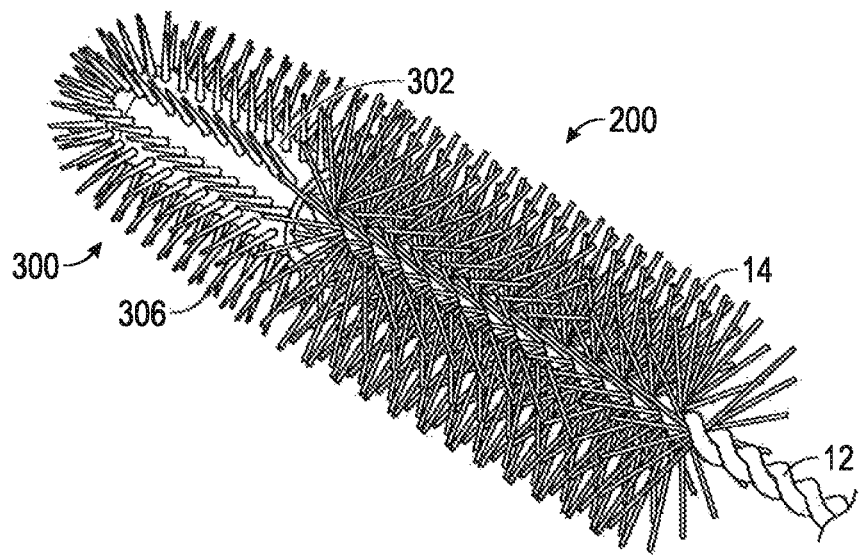
FIG. 11 is a perspective view of a twisted in wire brush having an alternative tip, according to an embodiment of the invention.
Figure 12:
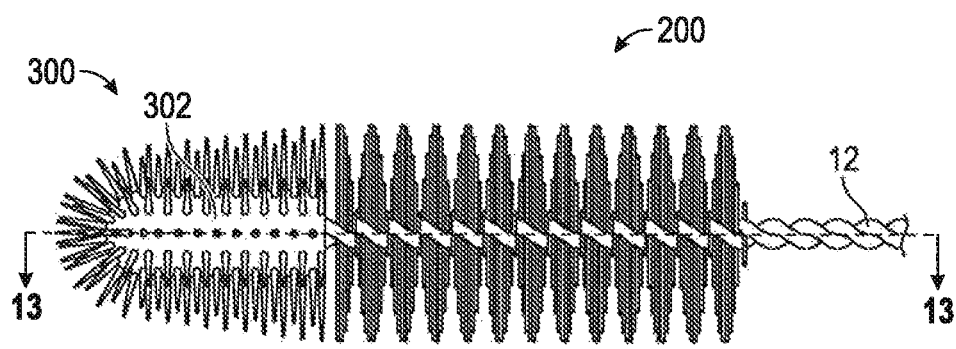
FIG. 12 is a side elevational view of the brush of FIG. 11.
Figure 13:
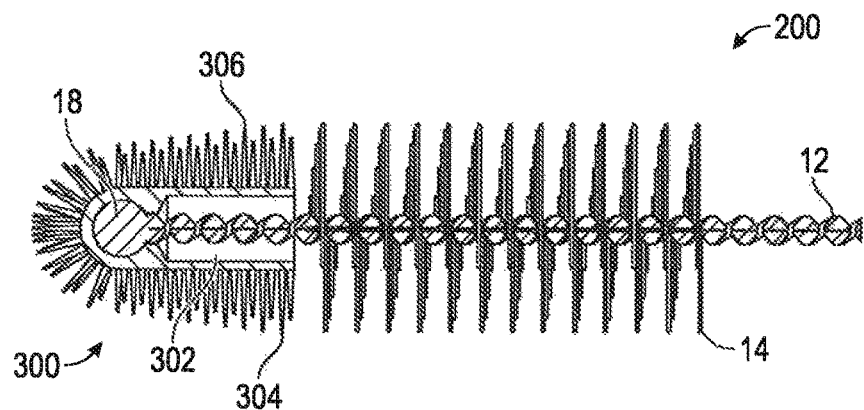
FIG. 13 is a cross-sectional view of the brush of FIG. 11, taken along line A-A of FIG. 12.

FIGS. 11-13 illustrate an alternative molded brush tip 300 attached to the spherical or ball-shaped tip 18 of a twisted in wire brush 200. The twisted in wire brush 200, is formed in the manner, and has the same configuration, as the twisted in wire brush discussed above. As shown therein, the brush tip 300 is a single molded piece having a core section 302 including a ball shaped socket 304 at a distal end thereof, and a plurality of bristles 306 connected to, and extending from, the core section 302. Like tip 16 described above, the socket 302 of the brush tip 300 is located at the distal end of the tip 300. As shown therein, the tip 18 of the brush 200 is received in the socket 304 of the brush tip 300 such that the assembled brush includes a bristle section 14 (with bristles held in place by the twisted core section 12 of the brush), and a bristle section 302 (with bristles formed in the molded tip 300).

Figure 14:
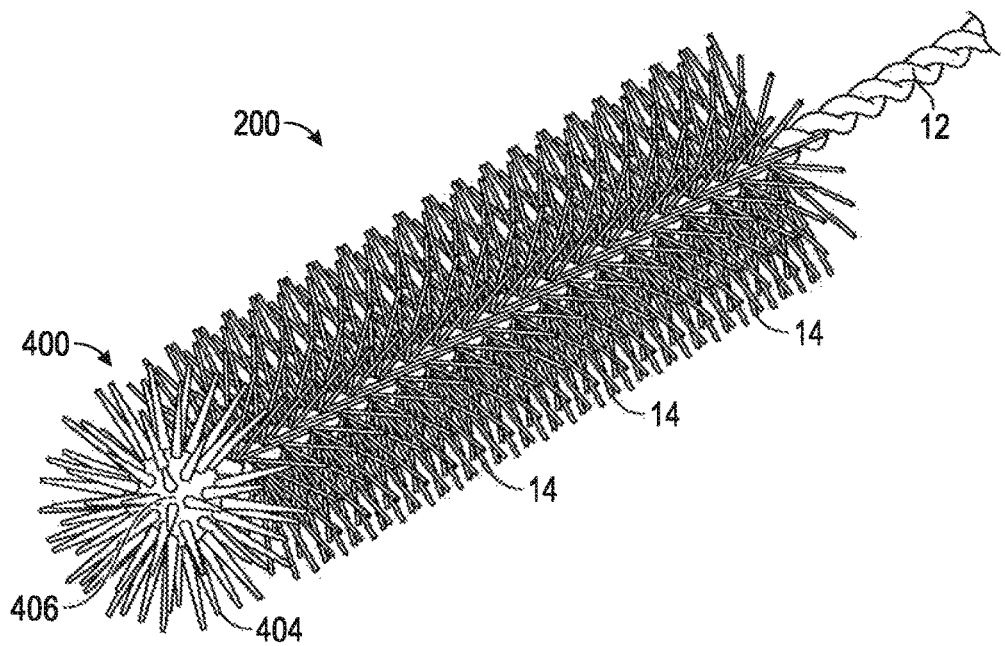
FIG. 14 is a perspective view of a twisted in wire brush having an alternative tip, according to an embodiment of the invention.

FIGS. 14-16 illustrate another molded brush tip 400 attached to the spherical or ball-shaped tip 18 of a twisted in wire brush 200. The twisted in wire brush 200, is formed in the manner, and has the same configuration, as the twisted in wire brush discussed above. As shown therein, the brush tip 400 is a single molded piece having a core section 402 defining a ball shaped socket 404, and a plurality of bristles 406 connected to, and extending from, the core section 402. The tip 18 of the brush 200 is received in the socket 404 of the brush tip 400 such that the assembled brush includes a bristle section 14 (with bristles held in place by the twisted core section 12 of the brush), and a bristle section 402 (with bristles formed in the molded tip 400).

Figure 17:
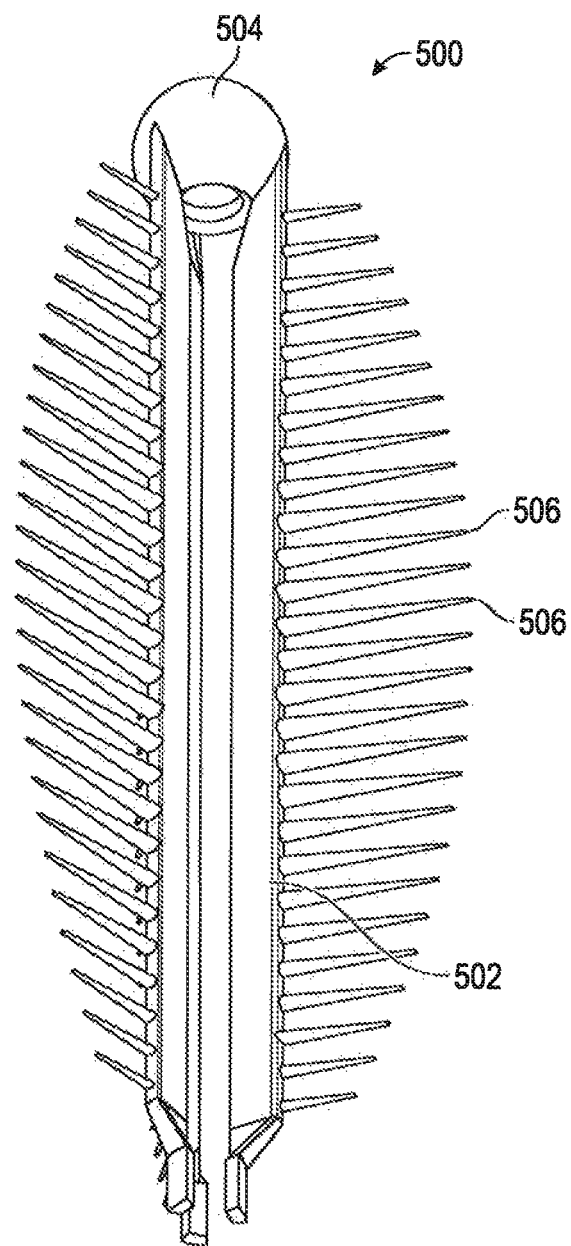

Turning now to FIGS. 17-19, a molded brush tip 500 according to another embodiment of the present invention is illustrated. As shown therein, the brush tip 500 is a single molded piece having a core section 502 including a ball shaped socket 504 at a distal end thereof, and a plurality of bristles 506 connected to, and extending from, the core section 502. Like tip 16 described above, the socket 502 of the brush tip 500 is located at the distal end of the tip 500.

Figure 20:
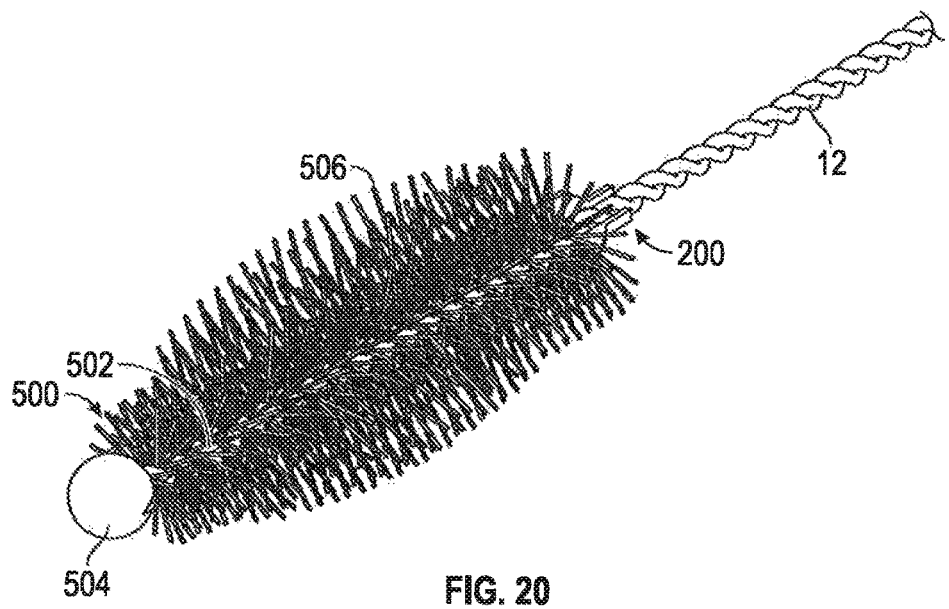
FIG. 20 is a side elevational view of the brush tip of FIG. 19.
Figure 21:
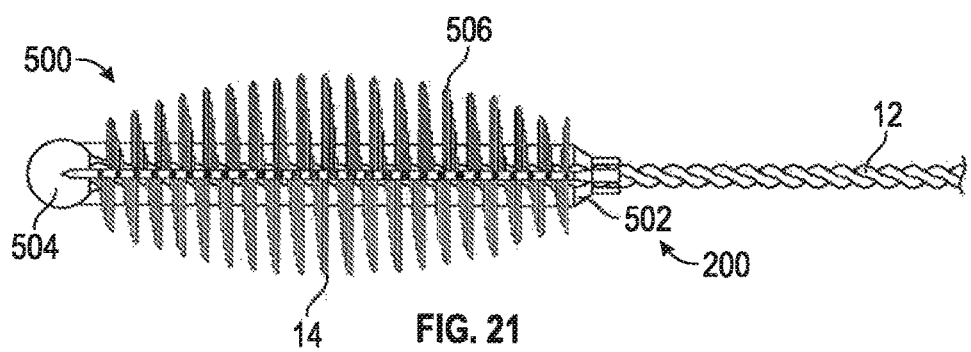
FIG. 21 is a cross-sectional view of the brush tip of FIG. 19, taken along line B-B of FIG. 20.
Figure 22:
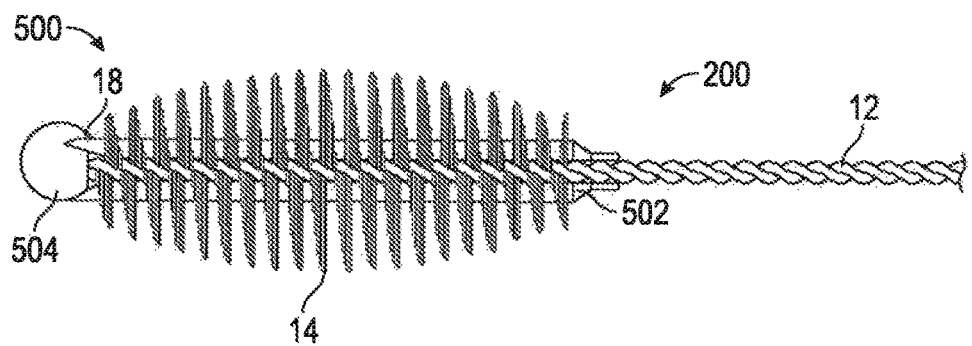

FIGS. 20-22 illustrate the brush tip 500 attached to the spherical or ball-shaped tip 18 of a twisted in wire brush 200. The twisted in wire brush 200, is formed in the manner, and has the same configuration, as the twisted in wire brush discussed above. As shown therein, the tip 18 of the brush 200 is received in the socket 504 of the brush tip 500 such that the assembled brush includes a bristle section 14 (with bristles held in place by the twisted core section 12 of the brush), and a bristle section 502 (with bristles formed in the core section 502 of the molded tip 500). In particular, as shown therein, the rows of bristles 506 of the tip 500 are received intermediate the bristles 14 of the twisted wire core 12 of the brush 200 to form a nesting or intermeshed arrangement of bristles.

Figure 23:
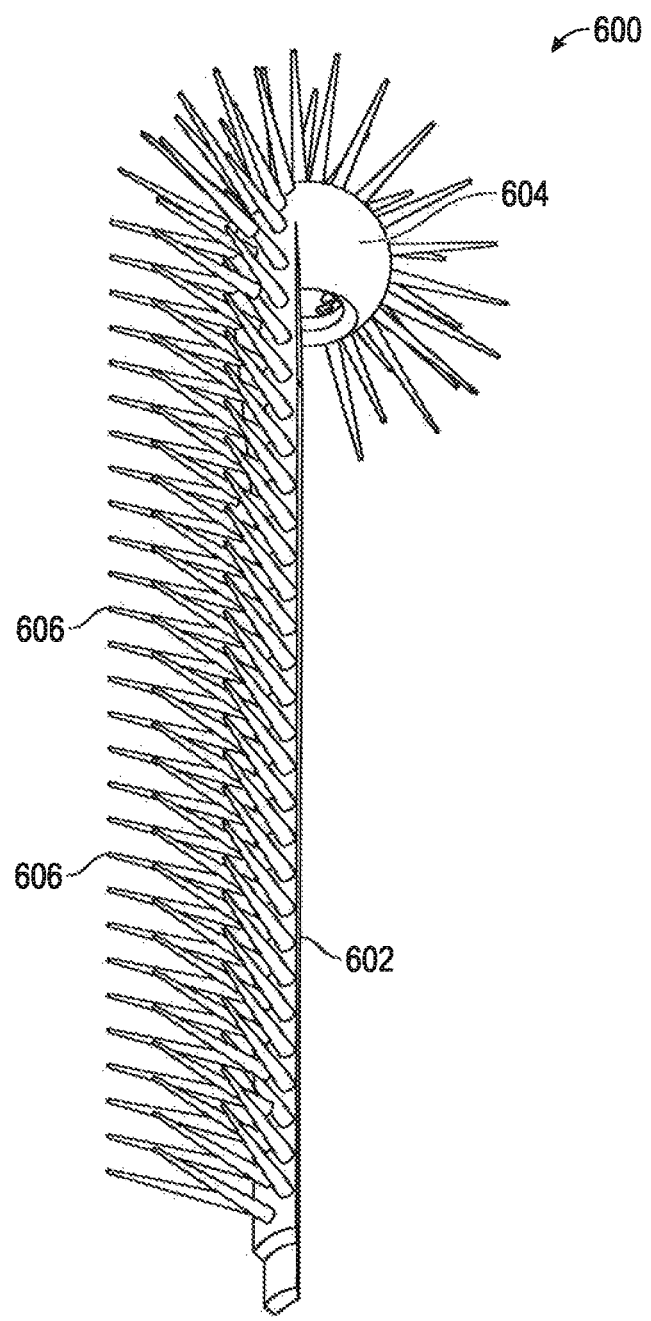
FIGS. 23-25 are various views of an alternative brush tip, according to an embodiment of the present invention.
Figure 24:
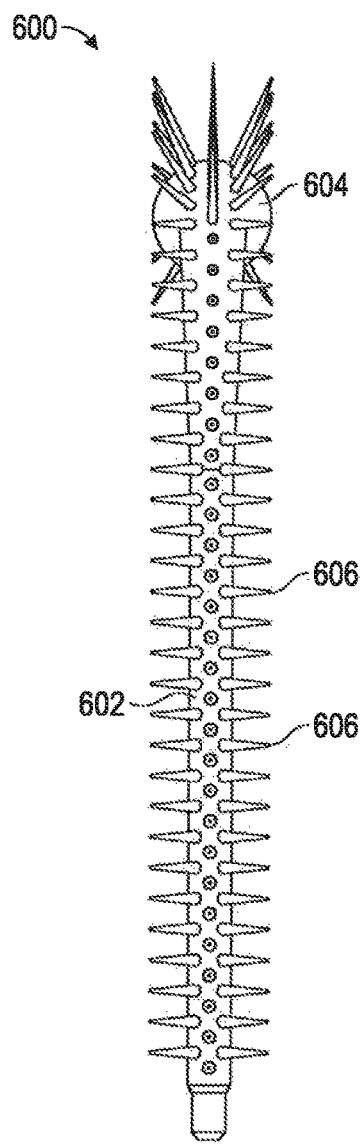
Figure 25:
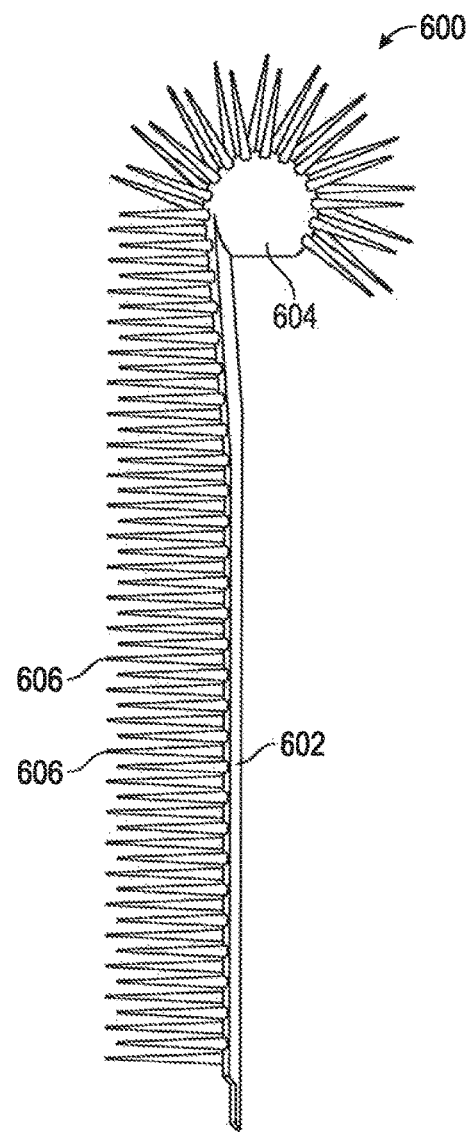

Turning finally to FIGS. 23-25, a molded brush tip 600 according to yet another embodiment of the present invention is illustrated. As shown therein, the brush tip 600 is a single molded piece having a core section 602 including a ball shaped socket 604 at a distal end thereof, and a plurality of bristles 606 connected to, and extending from, the core section 502. Like tip 16 described above, the socket 502 of the brush tip 600 is located at the distal end of the tip 600.

Figure 26:
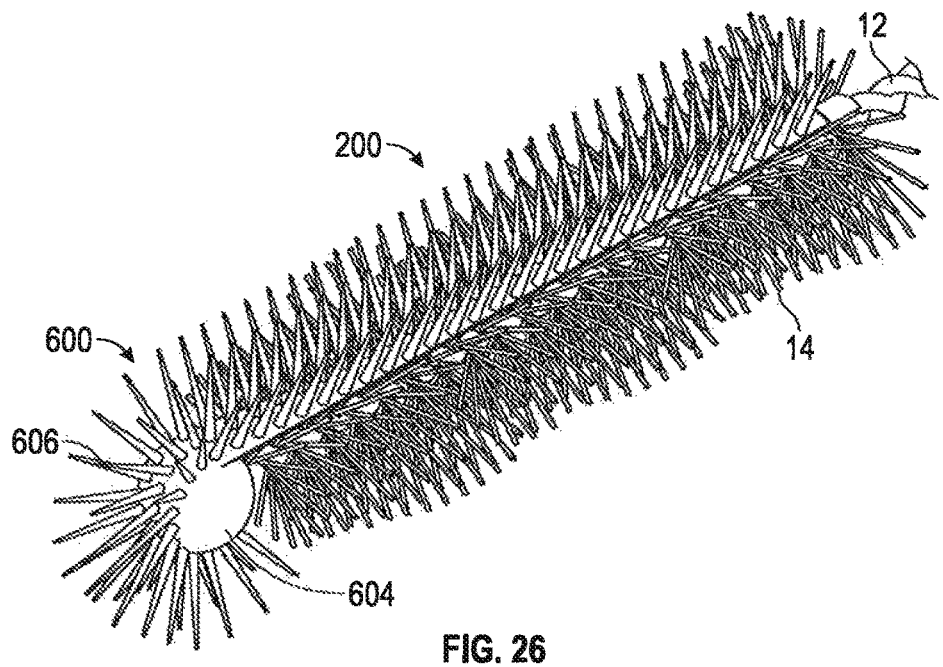
FIGS. 26-28 are various views of the brush tip of FIG. 23, shown attached to the rounded tip of a twisted in wire brush.
Figure 27:
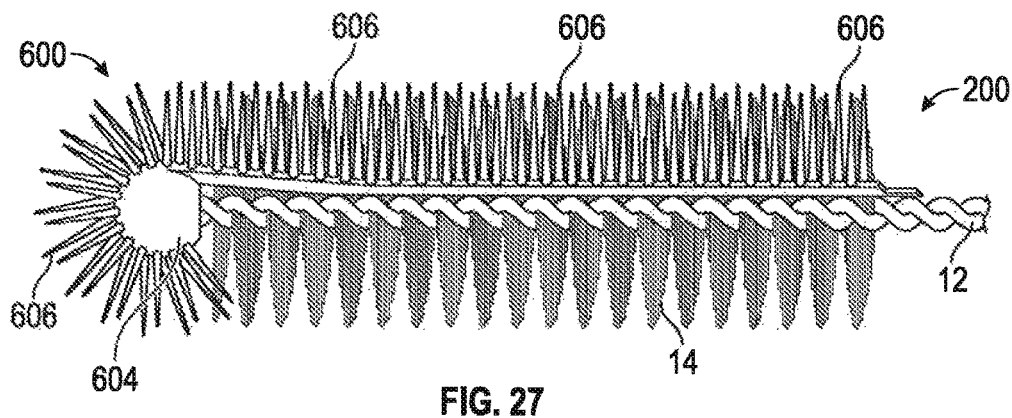
Figure 28:
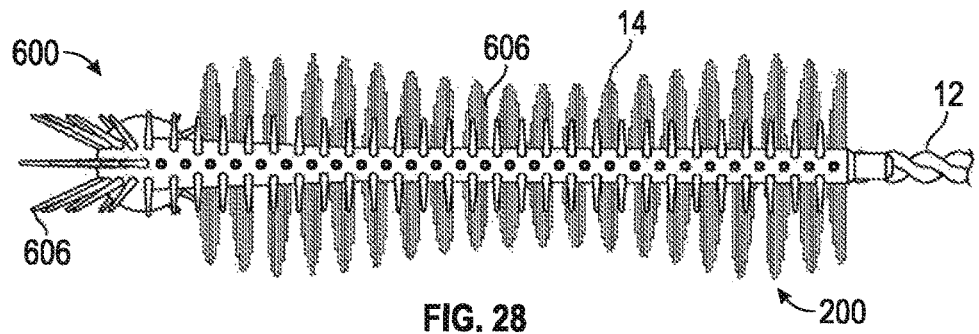

FIGS. 26-28 illustrate the brush tip 600 attached to the spherical or ball-shaped tip 18 of a twisted in wire brush 200. The twisted in wire brush 200, is formed in the manner, and has the same configuration, as the twisted in wire brush discussed above.

As shown therein, the tip 18 of the brush 200 is received in the socket 604 of the brush tip 600 such that the assembled brush includes a bristle section 14 (with bristles held in place by the twisted core section 12 of the brush), and a bristle section 602 (with bristles formed in the core section 602 of the molded tip 600). In particular, as shown therein, the row of bristles 606 of the tip 600 are received intermediate the bristles 14 of the twisted wire core 12 of the brush 200 to form a nesting arrangement of bristles. As will be readily appreciated, utilizing a tip 600 having this configuration of bristles 606 as an attachment to a twisted in wire brush 200 having an integral, rounded tip 18 allows the array of bristles in one part of the assembled brush to be denser than the bristles in other parts of the brush.

Turning finally to FIGS. 29-35, the present invention is not so limited as merely securing molded tips to the end of a twisted in wire brush. In particular, it is envisioned that the spherical tip may also be utilized as an anchoring point to link various accessories and devices to one another in a serial configuration. For example, as illustrated in FIGS. 29-35, the system and method of the present invention can be utilized to link multiple bristle sections to one another to form a device 700 for cleaning a longitudinal bore, such as the barrel of a firearm.

Figure 29:
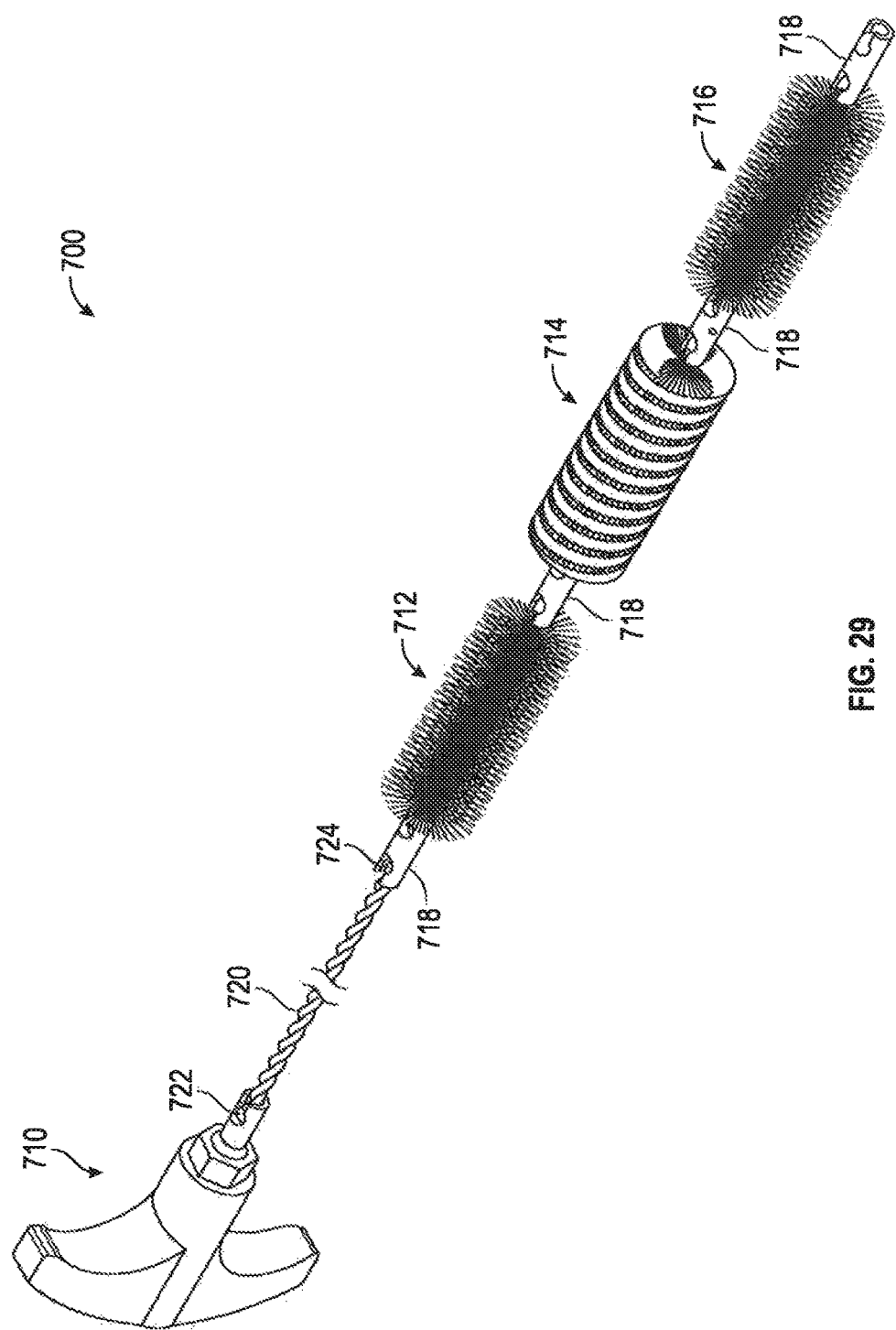
FIG. 29 is a perspective view of a brush according to another embodiment of the invention.

As shown in FIGS. 29 and 30, for example, the device 700 may include a handle 710 and a plurality of brushes (such as twisted in wire brushes 712, 714, 716) coupled to the handle 710 and linked end-to-end by a plurality of coupling or linking members 718. In an embodiment, the device 710 may also include a spacing element 720 (depicted in FIGS. 28 and 29 as a twisted wire core portion having spherical tips 722, 724 on the opposite ends thereof, formed in accordance with the process described hereinbefore) intermediate the brush 712 and the handle 710 for spacing the brushes 712, 714, 716 distal from the handle 710.

Figure 33:
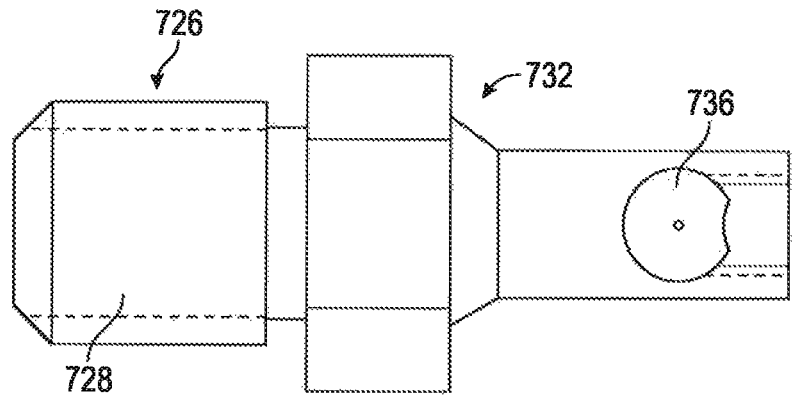
FIG. 33 is a side elevational view of the handle of the brush of FIG. 29.

With reference to FIGS. 31-33, the handle 710 may be a two part piece including a gripping member 726 having opposed arms 728, 730 and a threaded aperture configured to threadedly receive a correspondingly threaded stud or shaft 734 of a coupling member 732. Alternatively, the gripping member 726 and coupling member may be formed as a unitary component. As best shown in FIG. 32, the coupling member 732 includes a socket 736 located in an end of the coupling member 732 opposite the stud 734, and which is configured to receive therein the spherical tip or ball 722 on the proximal end of the spacing element 722 (or, alternatively, the spherical tip of a brush).

Figure 34:
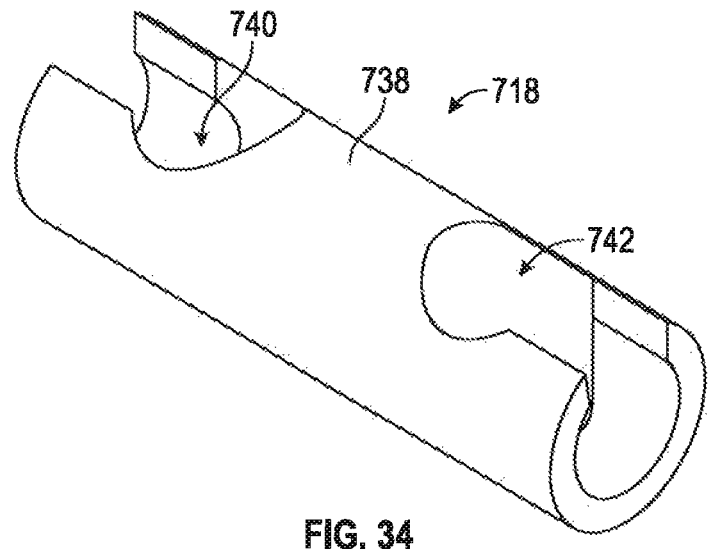
FIG. 34 is a perspective view of a linking element of the brush of FIG. 29.
Figure 35:
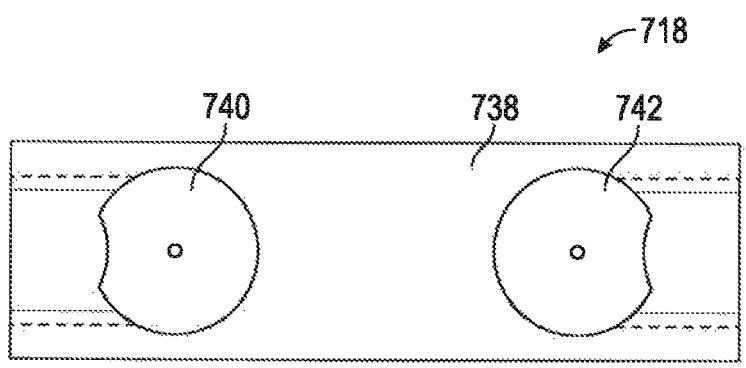
FIG. 35 is a side elevational view of the linking element of FIG. 34.

As illustrated in FIGS. 34 and 35, the linking members 718 each include a generally cylindrical body 738 having a pair of opposed recesses or ball-shaped sockets 740, 742 formed in the opposing ends thereof. The sockets 740, 742 are configured to receive therein the spherical, ball-shaped tip of either the spacing element 720, one of the brushes 712, 714, 716, or another accessory such as a squeegee or diaphragm. In an embodiment, the linking members 718, coupling member 732 and gripping member 726 may be formed from plastic or other polymer, although other materials known in the art may also be utilized without departing from the broader aspects of the invention.

Referring once again to FIGS. 29 and 30, the spacing element 720, brushes 712, 714, 716 and other accessories can each be manufactured to include a spherical tip 750 on one or both ends thereof in the manner discussed above (i.e., by welding or melting the end(s) of the wire core section of each such accessory or brush). The spacing element 720, brushes 712, 714, 716 and other accessories may then be linked serially, end-to-end by mating the spherical tips within the sockets of the linking members 718 to form a chain. The device 700 may then be inserted into a longitudinal bore, such as a gun barrel, and pulled through the bore for surface preparation or cleaning. In an embodiment, the brushes 712, 714, 716 may be more or fewer than three brushes, and can have different specifications from one another (e.g., different bristle densities, stiffness, thickness, bristle block diameters etc.) for providing different surface treatments. Importantly, this configuration allows any such device to be easily customized or adapted to perform a specific function by adding or subtracting brushes or accessories.

While the embodiments described above disclose and show the use of a mechanical fit, such as a snap fit or friction fit, to secure the spherical tip to a molded tip, linking member or coupling member, other redundant securing means may also be utilized without departing from the broader aspects of the present invention. For example, in certain embodiments, heat may be applied (such as to the molded tip or linking members) to slightly melt or heat-shrink the molded tip or linking members so that the internal passageway and/or socket therein more closely conforms to the ball-shaped end of the wire core. In addition, heat may be selectively applied to the molded tip to form prongs or projections that extend towards the core wire section to inhibit removal of the molded tip from the core wire section.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A brush, comprising:
a wire core having a proximal end and a distal end;
a round tip formed on said distal end of said wire core, said round tip being unitary with said wire core and being formed by melting or welding a portion of said wire core at said distal end; and
a molded tip attached to said wire core;
wherein said round tip of said wire core is received within a socket formed in a body of said molded tip to affix said molded tip to said wire core;
wherein said wire core includes at least two leg portions twisted about each other in a helical configuration;
wherein said brush includes a plurality of bristles anchored in said wire core between said leg portions and extending radially outward from said wire core;
wherein said round tip is a generally spherical tip; and
wherein said molded tip includes a plurality of bristles extending from said body.

2. The brush of claim 1, wherein:
said leg portions are formed from metal; and
said molded tip is formed from at least one of plastic and rubber.

3. The brush of claim 2, wherein:
said socket is located at a proximal end of said molded tip.

4. The brush of claim 2, wherein:
said socket is located at a distal end of said molded tip.

5. The brush of claim 1, wherein:
said spherical tip is made of existing material from said wire core without the addition of any other quantity of material.

6. The brush of claim 1, wherein:
at least a portion of said bristles of said molded tip are intermeshed with said bristles of said wire core.

7. The brush of claim 6, further comprising:
a second molded tip mounted to said second spherical tip of said wire core;
wherein said second spherical tip of said wire core is received within a socket formed in said second molded tip to affix said second molded tip to said wire core.

8. The brush of claim 1, further comprising:
a second spherical tip formed on said proximal end of said wire core, said second spherical tip being unitary with said wire core and being formed by melting or welding a portion of said wire core at said proximal end.

9. A brush, comprising:
a first brush member including a wire core having a proximal end and a distal end, and a generally spherical tip formed on at least one of said proximal end and said distal end of said wire core;
a second brush member including a wire core having a proximal end and a distal end, and a generally spherical tip formed on at least one of said proximal end and said distal end of said wire core; and
a linking member having a body having a first socket formed in a first end of said body and a second socket formed in a second end of said body;

wherein the generally spherical tip of said first brush member is received in said first socket of said linking member and the generally spherical tip of said second brush member is received in said second socket of said linking member such that said first brush member and said second brush member are linked together in a serial configuration.

10. The brush of claim 9, wherein:

said generally spherical tips of said first brush member and said second brush member are unitary with said wire core of said first brush member and said second brush member, respectively, and are formed by melting or welding a portion of said wire core of said first brush member and said second brush member, respectively.

11. The brush of claim 10, further comprising:

a handle having a socket;

a spacing element linked to said handle via a ball-and-socket connection, the spacing element having a first generally spherical tip at a proximal end formed by melting or welding said spacing element at said proximal end, and a second generally spherical tip at a distal end formed by melting or welding said spacing element at said distal end, said first generally spherical tip being received in said socket of said handle; and a second linking member linked to said spacing element and to said first brush via respective ball-and-socket connections;

wherein the second linking member has a first socket configured to receive said second generally spherical tip of said spacing element and a second socket configured to receive a second generally spherical tip of said first brush member;

wherein the handle, spacing element, first brush member and second brush member are linked end-to-end.

\* \* \* \* \*